United States Patent
Eger et al.

(10) Patent No.: US 8,939,148 B2
(45) Date of Patent: Jan. 27, 2015

(54) PROCESS FOR THE AUTOMATIC CONTROL OF A RESPIRATOR

(75) Inventors: Marcus Eger, Lübeck (DE); Hans-Ullrich Hansmann, Barnitz (DE); Tobias Glaw, Lübeck (DE); Frank Sattler, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 747 days.

(21) Appl. No.: 13/194,052

(22) Filed: Jul. 29, 2011

(65) Prior Publication Data

US 2012/0152250 A1 Jun. 21, 2012

(30) Foreign Application Priority Data

Dec. 20, 2010 (DE) .................... 10 2010 055 253

(51) Int. Cl.
*A61M 16/00* (2006.01)
*A61B 5/0488* (2006.01)
(Continued)

(52) U.S. Cl.
CPC .......... *A61M 16/0051* (2013.01); *A61B 5/0488* (2013.01); *A61B 5/087* (2013.01); *A61B 5/091* (2013.01); *A61M 2230/005* (2013.01); *A61M 2230/08* (2013.01); *A61M 2230/60* (2013.01)
USPC .................................................. 128/204.23

(58) Field of Classification Search
CPC ...... A61B 5/0488; A61B 5/087; A61B 5/091; A61M 16/0051; A61M 2230/60; A61M 2230/005; A61M 2230/08
USPC .......................... 128/200.24, 204.18–204.23, 128/204.26–204.28, 205.13–205.19, 128/205.23–205.25, 207.14–207.17, 898; 600/529, 534–536
See application file for complete search history.

(56) References Cited

U.S. PATENT DOCUMENTS 5,540,733 A * 7/1996 Testerman et al. .............. 607/42
5,551,418 A * 9/1996 Estes et al. ............... 128/204.23

(Continued)

FOREIGN PATENT DOCUMENTS

DE 699 21 782 T2 10/2005
DE 10 2007 062 214 B3 8/2009

(Continued)

OTHER PUBLICATIONS

Merlett, R., Parker P. A.: Electromyography. Physiology, Engineering, and Noninvasive Applications. IEEE Press, Wiley Interscience, 2004, starting from chapter 6.4 or pp 139 ff.

*Primary Examiner* — Tan-Uyen (Jackie) T Ho
*Assistant Examiner* — Mark K Han
(74) *Attorney, Agent, or Firm* — McGlew and Tuttle, P.C.

(57) ABSTRACT

A process is provided for the automatic control of a respirator for changing over (triggering) between consecutive phases of respiration (inspiration and expiration phases), wherein a pneumatic breathing activity signal $u_{pneu}(t)$ and a non-pneumatic breathing activity signal $u_{non-pneu}(t)$ of a patient are picked up. The intervals $\Delta_{pneu}(t)$ and $\Delta_{non-pneu}(t)$ to the associated threshold variables are respectively determined starting from a preset reference point in time since the beginning of the present phase of respiration. The intervals are standardized to one another at $\delta_{pneu}(t)$ and $\delta_{non-pneu}(t)$, such that the intervals have equal interval values at a preset reference point in time. The standardized intervals $\delta_{pneu}(t)$ and $\delta_{non-pneu}(t)$ are averaged to a mean interval indicator and a changeover is made into the next phase of respiration when the combined interval indicator is 0.

20 Claims, 6 Drawing Sheets

(51) Int. Cl.
*A61B 5/087* (2006.01)
*A61B 5/091* (2006.01)

(56) References Cited

U.S. PATENT DOCUMENTS

| | | | |
|---|---|---|---|
| 5,820,560 A | 10/1998 | Sinderby et al. | |
| 6,588,423 B1 | 7/2003 | Sinderby | |
| 6,907,881 B2 * | 6/2005 | Suki et al. | 128/204.21 |
| 7,100,607 B2 * | 9/2006 | Zdrojkowski et al. | 128/204.18 |
| 8,439,034 B2 * | 5/2013 | Decker et al. | 128/204.23 |
| 2006/0272641 A1 * | 12/2006 | Madaus et al. | 128/204.21 |
| 2008/0099019 A1 * | 5/2008 | Martin et al. | 128/205.23 |
| 2008/0281219 A1 * | 11/2008 | Glickman et al. | 600/533 |
| 2009/0159082 A1 * | 6/2009 | Eger | 128/204.23 |
| 2010/0083968 A1 * | 4/2010 | Wondka et al. | 128/204.23 |
| 2010/0180898 A1 * | 7/2010 | Schneider et al. | 128/204.23 |
| 2010/0252038 A1 * | 10/2010 | Lagerborg et al. | 128/204.23 |

FOREIGN PATENT DOCUMENTS

| | | |
|---|---|---|
| WO | 99/43374 A1 | 9/1999 |
| WO | 2008131798 A1 | 11/2008 |

* cited by examiner

PROCESS FOR THE AUTOMATIC CONTROL OF A RESPIRATOR

CROSS REFERENCE TO RELATED APPLICATIONS

This application claims the benefit of priority under 35 U.S.C. §119 of German Patent Application DE 10 2010 055 253.4 filed Dec. 20, 2010, the entire contents of which are incorporated herein by reference.

FIELD OF THE INVENTION

The present invention pertains to a process for the automatic control of a respirator for changing over (triggering) between alternately consecutive phases of respiration (phases of inspiration and expiration), in which a pneumatic breathing activity signal $u_{pneu}(t)$ and a non-pneumatic breathing activity signal $u_{non-pneu}(t)$ of a patient are picked up.

BACKGROUND OF THE INVENTION

Artificial respiration with respirators is aimed at relieving the respiratory muscles of a patient and at guaranteeing a sufficient supply of oxygen and elimination of carbon dioxide. This can happen by complete takeover of the breathing activity by the respirator or in an assisting process by partial takeover of breathing activity by the respirator, whereby in the latter assisting process, a present breathing activity of the patient is assisted or reinforced. For this, the respirators contain a fan or a compressed gas supply for supplying breathing gas with a pressure, which is preset by a control unit. Furthermore, sensors are present that detect pneumatic breathing signals in a time-dependent manner, for example, airway pressure, volume flow (flow) of the breathing gas and volume (which results from the integration of the flow), and forward these to the control unit.

In view of the rise in chronic lung diseases and the demand for an improved therapy, noninvasive breathing assistance with improved interaction of the patient and respirator is a decisive requirement of modern respirators. An essential object herein is to establish time-based synchronicity between the device-side assistance and the patient's own breathing activity. Spontaneously breathing patients were frequently sedated in the past to adjust the respiration correctly and to force synchronicity between patient and respirator. This procedure is no longer acceptable by today's knowledge since risks of lung damage caused by the respiration have to be dealt with.

For an improved synchronization between the breathing activity of the patient and the fan action, it is important to detect the beginning of inspiration and the beginning of expiration in the breathing activity of the patient in a reliable manner. Breathing phase detection is especially often incorrect in newborns and in Chronic Obstructive Pulmonary Disease (COPD) patients using conventional processes and leads to increased respiratory work until exhaustion.

For an artificial respiration which shall take the patient's breathing activity into consideration in an improved manner, it is known from DE 10 2007 062 214 B3 to pick up electromyographic signals, besides pneumatic breathing activity signals, by means of electrodes placed on the thorax and to derive electromyographic breathing activity signals (EMG signals) therefrom. These EMG signals are independent of the pneumatic breathing activity signals and therefore represent an independent source of information, which can be used to detect the beginning of inspiration and expiration. The EMG signals are, however, not infrequently superimposed by interference, for example, the ECG signal of the heart, motion artifacts or so-called cross-talk (muscle activity that has nothing to do with the respiratory system of the patient).

For the last-mentioned reason, EMG signals cannot be used easily as a sole basis for the detection of the beginning of inspiration and expiration and the corresponding control of the respirator. In this connection, a changeover between signal sources is known in the sense that a changeover is made between conventionally used pneumatic breathing activity signals (usually volume flow or pressure) and EMG signals depending on signal quality, whereby the signal quality is detected, for example, by determining a signal/noise ratio. Such a changeover between the respiration control on the basis of EMG signals and on the basis of other breathing activity signals is described in WO 2008/131798 A1. Therein, a changeover is made from a control based on the EMG signals to a control based on other breathing activity signals when a lack of synchronicity is found between the EMG signal and breathing activity. As soon as sufficient synchronicity is found again between EMG signal and breathing activity, the respirator returns again into the operating mode based on EMG signals. However, the contribution of a signal source is basically completely ignored in such a changeover, such that consequently independent information gets lost. This is especially a drawback then, when the quality of both signal sources is low.

A triggering of breaths on the basis of EMG signals is described in U.S. Pat. No. 6,588,423 B1. Here, the EMG raw signal is preprocessed and is finally checked for triggering an intensity indicator (root mean square) of the EMG signal, whereby the exceeding of a fixed threshold is used as a threshold criterion.

SUMMARY OF THE INVENTION

An object of the present invention is to provide an automatic process for changing over into the next phase of respiration in a respirator, which reacts more sensitively and earlier to breathing efforts, without incorrectly increasingly triggering a transition into the next phase of respiration in the case of interference.

According to the process of the present invention, a pneumatic breathing activity signal $u_{pneu}(t)$ and a non-pneumatic breathing activity signal $u_{non-pneu}(t)$ of a patient are detected. A pneumatic breathing activity signal is defined here as a measured signal that directly concerns the control of pneumatic breathing, for example, pressure, volume flow (flow) or volume. In addition, a non-pneumatic breathing activity signal is detected, which represents the state of the respiratory system and the breathing activity for the patient, e.g., an electromyographic signal (EMG signal), which is picked up via electrodes placed on the thorax, or respiratory muscle pressure calculated by means of a model. For these two independent signals, the intervals $\Delta_{pneu}(t)$ and $\Delta_{non-pneu}(t)$ to associated threshold variables, which indicate the transition into the next phase of respiration, are determined starting from a given reference point in time in the phase of respiration (e.g., 200 msec after the beginning of the phase of respiration). These intervals to the associated threshold variables are then standardized to one another, such that the two intervals can be compared directly with one another, which is achieved by their being standardized at the reference point in time to the same interval values; exemplary formulas are given for this further below. Consequently, the two intervals $\Delta_{pneu}(t)$ and $\Delta_{non-pneu}(t)$ are standardized to the same value at $\delta^{pneu}(t)$ and $\delta_{non-pneu}(t)$ at the reference point in time. These standardized intervals of the threshold variables are finally averaged to a mean interval indicator or combined and the changeover is made into the next phase of respiration when the combined interval indicator is 0. A plurality of non-pneumatic -breathing activity signals $u_{non-pneu,i}(t)(i=1,\ldots n)$ of a patient may be detected, and an interval $\Delta_{non-pneu,i}(t)$ and a standardized interval $\delta_{pneu,i}(t)$ may be determined for each, respectively, and all intervals $\delta_{pneu}(t)$ and $\delta_{non-pneu,i}(t)$ may be averaged to a mean interval indicator and a changeover may be made into the next phase of respiration when the combined interval indicator is 0.

The use of combined interval indicators for detecting the beginning of inspiration and expiration is characterized by higher robustness with faster detection at the same time. As a result, a triggering or control signal can be derived for the respirator, which represents, with minimal necessary delay, the highest possible content of information for patient activity and hence it makes possible a more reliable assistance of breathing than previously possible. In the state of the art, various criteria are combined with one another only in this respect for triggering phases of respiration, which gives priority to the chronologically first-met criterion and thereupon brings about the changeover ("first come—first served"), i.e., a threshold value comparison is performed on each signal and already the beginning of the phase of respiration is triggered when the criterion is met. This procedure has a drawback because the reliability of the breathing activity signals is not taken into consideration in comparison to their threshold variables. Therefore, it was possible in the state of the art that the chronologically first met threshold value criterion brings about an early triggering of the beginning of the phase of respiration, even though the breathing activity signal bringing about this triggering is possibly less reliable and disturbed by artifacts.

By combining the intervals to the threshold values of a pneumatic breathing activity signal and a non-pneumatic breathing activity signal according to the present invention, information content and thus reliability of the changeover into the next phase of respiration are considerably increased, since at least two essentially uncorrelated breathing activity signals (i.e., the interference in one signal does not usually develop in the other signal) go into the combined interval indicator. While pneumatic breathing activity signals have a more or less great correlation with one another (sources of interference have the same effect in all pneumatic signals), an independent source of information can be added by adding a non-pneumatic breathing activity signal, which considerably increases the reliability of the correct detection of the beginning of the phase of respiration. If, for example, one of the two breathing activity signals is impaired by an interference, such that reaching the associated threshold variable is simulated, then the second breathing activity signal uncorrelated with the first signal will usually still have a considerable deviation from its threshold variable, such that the combined interval indicator is still sufficiently removed from 0, so that no premature beginning of the next phase of respiration is triggered. The combined interval indicator may be determined by the equation:

$$K(t) = \sum_{i=1}^{n} \frac{Q_{non-pneu i}}{\sum_{j=1}^{n} Q_{non-pneu,j} + Q_{pneu}} \cdot \delta_{non-pneu i}(t) +$$

-continued $$\frac{Q_{pneu}}{\sum_{j=1}^{n} Q_{non-pneu,j} + Q_{pneu}} \cdot \delta_{pneu}(t),$$

wherein $Q_{pneu}$ is a quality indicator for the pneumatic, breathing activity signal and $Q_{non-pneu,i}$ is a quality indicator for the non-pneumatic breathing activity signal $u_{non-pneu,i}(t)(i=1,\ldots n)$.

The reference point in time is used to provide a minimal delay to the beginning of the current phase of respiration. This delay shall be so short that the probability that a change into the next phase of respiration could take place within this delay time after the beginning of a phase of respiration is already again very low. This is given at a reference point in time of 200 msec. It is then sufficient to determine the standardized intervals to the threshold variables starting from this reference point in time and to process and observe same in order to then later trigger the change to the next phase of respiration.

The pneumatic breathing activity signal is preferably selected from among the signals for airway pressure, flow, and volume. The non-pneumatic breathing activity signal is selected from signals that represent the status of the respiratory system and breathing activity for the patient. Besides the calculated respiratory muscle pressure, measured esophageal pressure and pressure over the stomach, these are electric signals, in particular EMG signals, MMG signals (mechanomyographic signals), thoracic impedance signals, Fujitsu Enhanced Imaging Technology (FEIT) signals, geometric signals, and in particular chest belt signals, abdominal belt signals and strain gauge signals, motion signals, in particular acceleration sensor signals, and acoustic signals, and in particular microphone signals. These non-pneumatic breathing activity signals thus refer to the internal pressure conditions for the patient, which are connected to breathing activity, electric activity that is connected to breathing activity, change in geometric size in the thoracic area that is connected to breathing activity, motion in the area of the thorax that is connected to breathing activity, or acoustic activity that is connected to breathing activity. These breathing activity signals are not correlated with the pneumatic breathing activity signals, which are detected by the respirator, in the sense that an artifact or an interference in one signal would also result in an interference in the other signal. Based on this independence of the pneumatic and non-pneumatic breathing activity signals, a greater information content is available in the assessment of the intervals to the threshold variables, such that the changeover can be done at the beginning of the next phase of respiration with higher sensitivity, but at the same time not with increased susceptibility to interference.

The standardized interval to the threshold variable for the pneumatic breathing activity signal can be determined, for example, by $$\delta_{pneu}(t) = \frac{u_{pneu}(t) - u_{pneu,thresh}(t)}{u_{pneu ref} - u_{pneu,thresh}(t)},$$

wherein $U_{pneu\ ref}$ is the pneumatic breathing activity signal value at a preset reference point in time of the present phase of respiration. Numerators and denominators are equal at the reference point in time of the present phase of respiration, and the standardized interval at the reference point in time 1.

In the above-mentioned formula, the threshold $u_{pneu,thresh}(t)$ is given as time-dependent; it is also possible to work with a chronologically constant threshold; however, it is generally also possible to use so-called dynamic thresholds, which vary as a function of time and will still be described further below.

The standardized interval to the threshold variable for the non-pneumatic breathing activity signal can be determined, for example, by $$\delta_{non-pneu}(t) = \frac{u_{non-pneu}(t) - u_{non-pneu,thresh}(t)}{u_{non-pneuref} - u_{non-pneu,thresh}(t)},$$

wherein $u_{non-pneu\ ref}$ is the non-pneumatic breathing activity signal at the preset reference point in time after the beginning of the phase of respiration.

The flow signal V(t) is preferably used as the pneumatic breathing activity signal, such that the standardized interval of the associated threshold variable is determined by $$\delta \dot{V}(t) = \frac{\dot{V}(t) - \dot{V}_{thresh}(t)}{\dot{V}_{ref} - \dot{V}_{thresh}(t)},$$

wherein
$\dot{V}_{ref}$ is the value of the flow signal at the preset reference point in time.

An electromyographic signal EMG(t) is preferably used as the non-pneumatic breathing activity signal, such that the standardized interval to the associated threshold variable is determined by $$\delta EMG(t) = \frac{EMG(t) - EMG_{thresh}(t)}{EMG_{ref} - EMG_{thresh}(t)},$$

wherein $EMG_{ref}$ is the EMG signal at the preset reference point in time in the phase of respiration.

It can be seen that the standardization of the intervals to the associated threshold variables is such that the intervals of the non-pneumatic breathing activity signal and of the pneumatic breathing activity signal at the reference point in time are equal in the previous phase of respiration, and in particular 1 in the present case.

For averaging the intervals of the pneumatic and non-pneumatic breathing activity signals to their associated threshold values, it is possible to determine by weighted averaging as weighted arithmetic, geometric or harmonic average, as weighted median or as minimum or maximum.

For a weighted averaging to determine the combined interval indicator, quality indicators for the breathing activity signals can be used, for example, as follows:

$$K(t) = \frac{Q_{non-pneu}}{Q_{non-pneu} + Q_{pneu}} \cdot \delta_{non-pneu}(t) + \frac{Q_{pneu}}{Q_{non-pneu} + Q_{pneu}} \cdot \delta_{pneu}(t),$$

wherein $Q_{pneu}$ is a quality indicator for the pneumatic breathing activity signal and $Q_{non-pneu}$ is a quality indicator for the non-pneumatic breathing activity signal. Examples of quality indicators are given further below.

A preprocessed EMG signal is preferably used. Such a preprocessing of the EMG raw signal takes place in the known manner in such a way that the EMG raw signal is freed from interference signals (e.g., ECG, motion artifacts, hum-ming) and finally an envelope detection is performed. An envelope detection may be done, for example, by "rectification" and subsequent low-pass filtering, whereby the "rectification" is done by an operation imaging the quantity (e.g., by squaring or pure quantity formation). After a low-pass filtering, the envelope is obtained, i.e., the curve enveloping the signal pattern of the raw signal. A preferred realization of envelope detection is the formation of the so-called RMS (Root Mean Square) over the length of a sliding time window. The concept of EMG amplitude estimation, which is defined by the term "envelope detection," is described in detail in Merlett, R., Parker P. A.: Electromyography. Physiology, Engineering, and Noninvasive Applications. IEEE Press, Wiley Interscience, 2004, starting from chapter 6.4 or pages 139 ff (the contents of which are incorporated herein by reference).

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
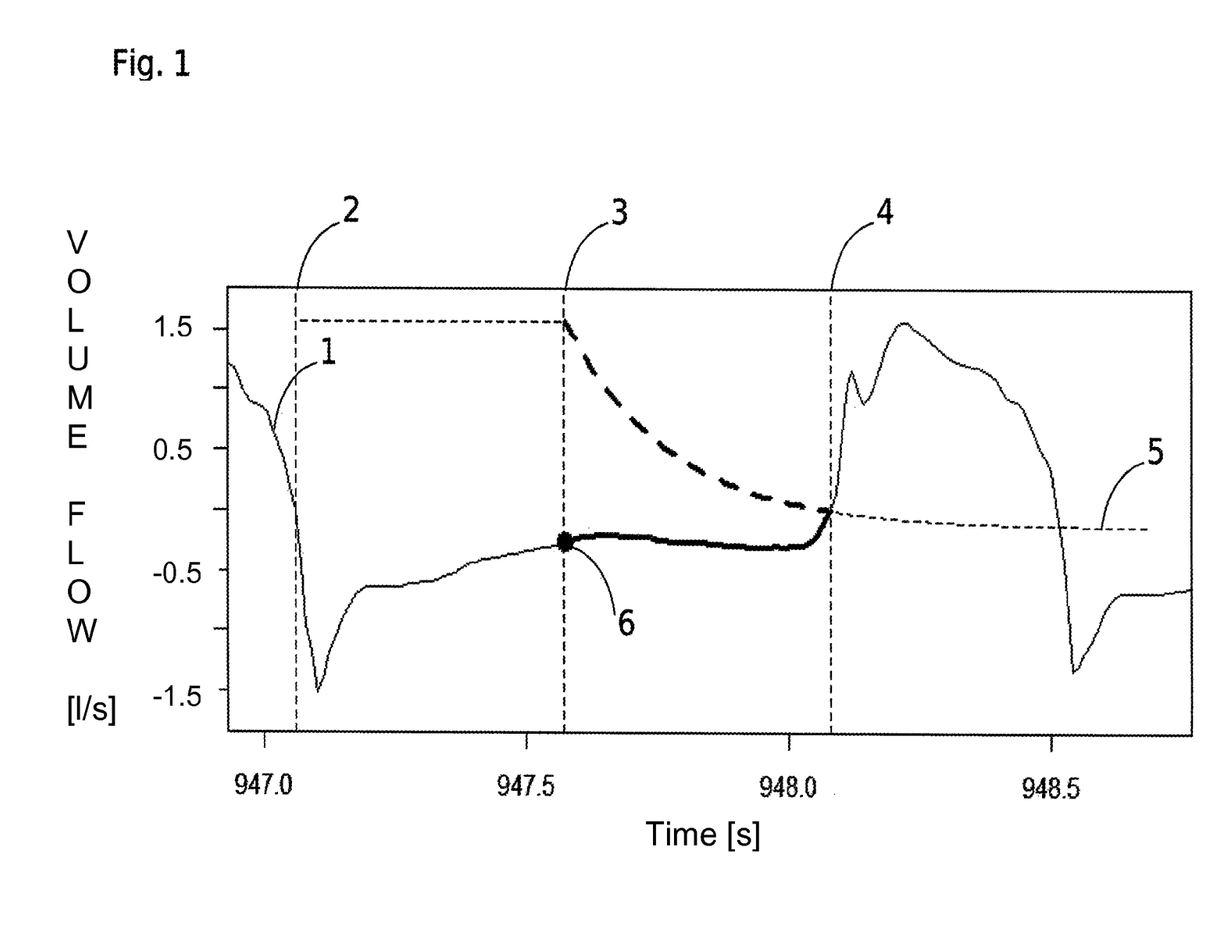
FIG. 1 is a graph of a pneumatic breathing activity signal, in particular the volume flow, as a function of time over an expiration, a full inspiration and the beginning of another expiration.

Referring to the drawings in particular, FIG. 1 shows the volume flow as a pneumatic breathing activity signal as a function of time for a period, which shows the end of an inspiration, a next full expiration, a next full inspiration and the beginning of the next expiration. The volume flow signal is provided with the reference number 1. At the point in time 2, a changeover is made into the phase of expiration by meeting the still to be described criteria. At this point in time, the threshold variable is also reset, which shall be used for changing over into the next inspiration. In this exemplary embodiment, the work is carried out with a so-called dynamic threshold rather than with a fixed threshold value (which would be a horizontal straight line in FIG. 1). In the present case, a dynamic threshold is suitable for detecting the next inspiration, which, at the beginning of an expiration, begins at first with a relatively high value for a preset period of time and is then lowered to a target value, which will be reached at the expected point in time of the end of expiration; the expected endpoint of expiration may be estimated, for example, from the duration of the past expiration phases. The preset period of time, for which the threshold is maintained at a relatively high constant value after the beginning of expiration, will be selected, such that it is markedly shorter than all expected expiration phases, i.e., the probability that a new inspiration already begins during the period of time should be very low; such a period of time may be, e.g., 200 msec. The target value of the threshold can be derived, e.g., from the maximum values and minimum values of the signals $u_{pneu}^{max}$ and $u_{pneu}^{min}$ and $u_{mnon-pneu}^{max}$ and $u_{non-pneu}^{min}$ in previous phases of respiration.

Inversely, the threshold begins for the detection of the next expiration when an inspiration begins with a low value for a preset period of time and is then raised to a preset target value, which will be reached at the expected point in time of the end of the inspiration. The expected endpoint of the inspiration can in turn be estimated from the duration of the past inspiration phases and the target values can be derived from the maximum values and minimum values signals $u_{pneu}^{max}$ and $u_{pneu}^{min}$ and $u_{mnon-pneu}^{max}$ and $u_{non-pneu}^{min}$ in previous phases of respiration.

The idea, on which such dynamic thresholds are based, is that, right after the beginning of a phase of respiration, the probability is very low that a change into the next phase of respiration could already take place again within the preset short period of time. Therefore, it is possible to work with set thresholds at the beginning of a phase of respiration such that an incorrect changeover is almost ruled out even in case of great interference, while, after the preset period of time, the threshold is brought to a target value, which will be reached at the expected end of the phase of respiration, such that the beginning of the next phase of respiration can be detected with high sensitivity. The expected value may correspond to the value that is suitable for a sensitive constant threshold. In this respect, towards the end of the phase of respiration, a sensitive triggering is guaranteed, at the beginning of which, however, a mistriggering due to interference is suppressed.

If it were triggered only on the basis of the pneumatic breathing activity signal, the next phase of inspiration would be triggered when reaching the threshold 5 by the breathing activity signal 1 at the point in time 4. According to the present invention, however, no threshold criterion related to a single signal is applied, but rather combined threshold criteria, which are based on different breathing activity signals.

Figure 2:
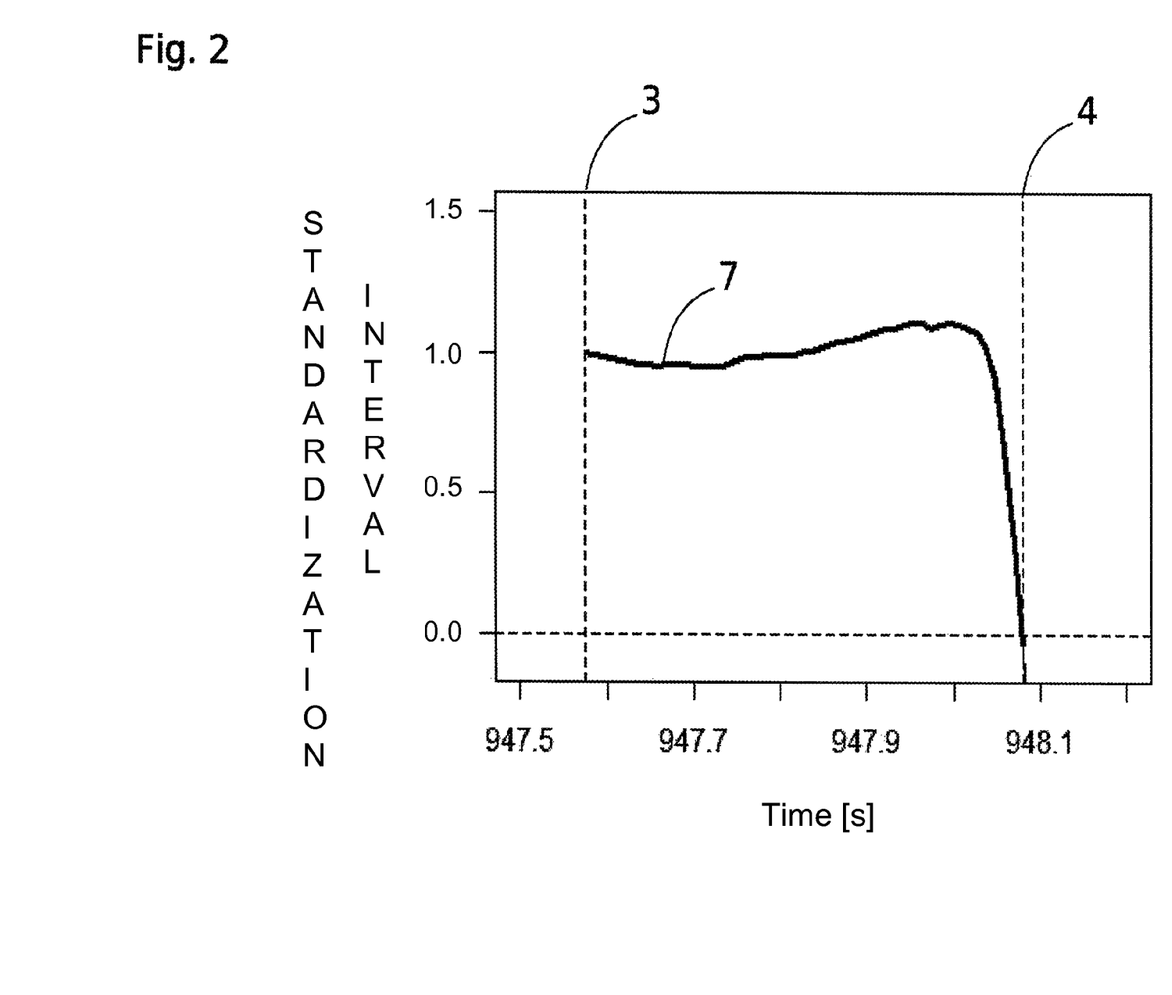
FIG. 2 is a graph of a standardized interval indicator for the pneumatic breathing activity signal from FIG. 1 at its threshold variable.

FIG. 2 shows the interval of the volume flow signal 1 of the dynamic threshold 5 from FIG. 1 after standardization as standardized interval indicator $\delta_{pneu}(t)$ over an expiration phase (7). The interval indicator $\delta_{pneu}(t)$ is determined starting from the reference point in time in the phase of respiration. The standardization takes place such that the present interval of the volume flow signal 1 of the dynamic threshold 5 through the interval of the value of the volume flow signal at the preset reference point in time of the present phase of respiration of the dynamic threshold is standardized to the equal value, in particular 1:

$$\delta_{pneu}(t) = \frac{u_{pneu}(t) - u_{pneu,thresh}(t)}{u_{pneu\ ref} - u_{pneu,thresh}(t)}.$$

Such a preset reference point in time is designated by 3 in FIG. 1 and the corresponding value of the volume flow signal is designated by 6. At this point in time, the pneumatic and non-pneumatic intervals are standardized to an equal value.

Figure 3:
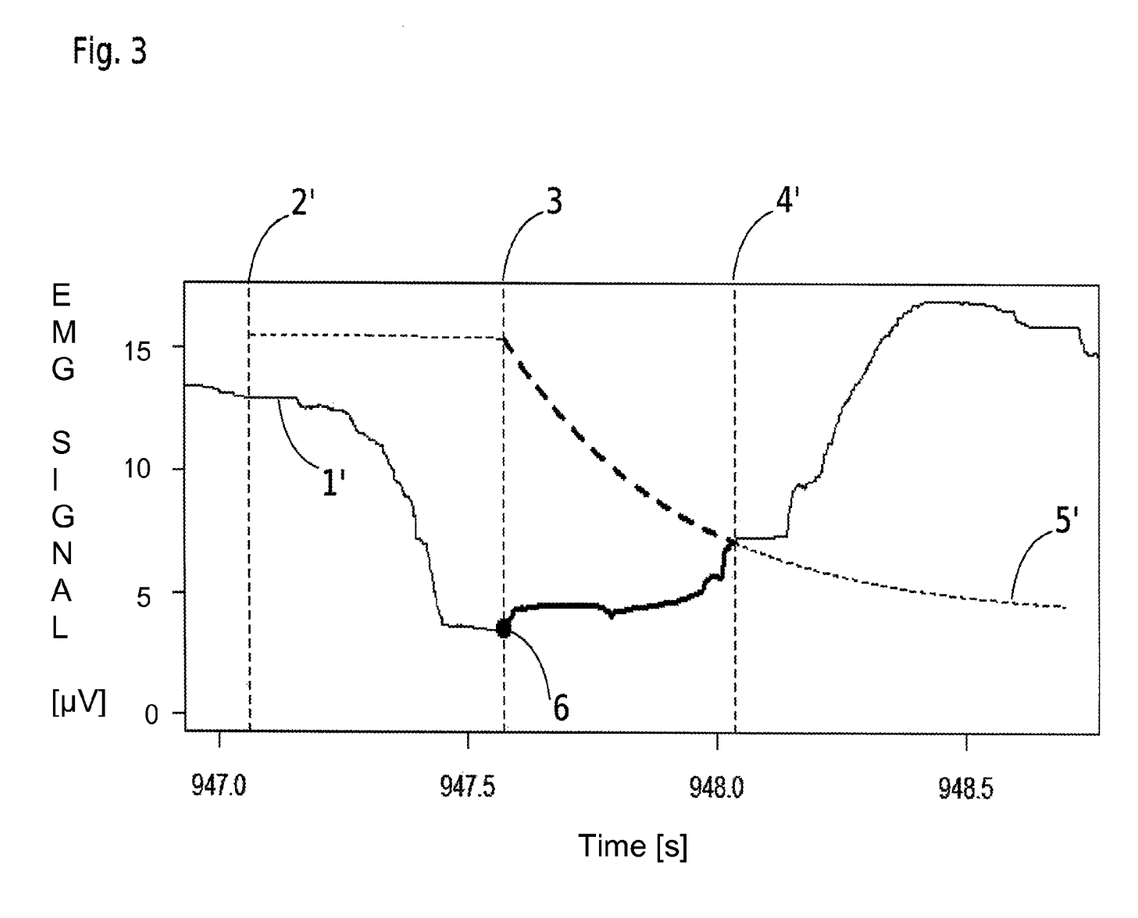
FIG. 3 is a graph of a non-pneumatic breathing activity signal, in particular an EMG signal, as a function of time over the same period as in FIG. 1.

FIG. 3 shows the non-pneumatic breathing activity signal for the same period of as in FIG. 1 as a function of time. The EMG signal is designated by 1'. The beginning of the expiration phase is indicated by 2', the preset short period after the beginning of the expiration phase, at changeover 2, by 3', after which the initially high constant dynamic threshold 5' is lowered.

Figure 4:
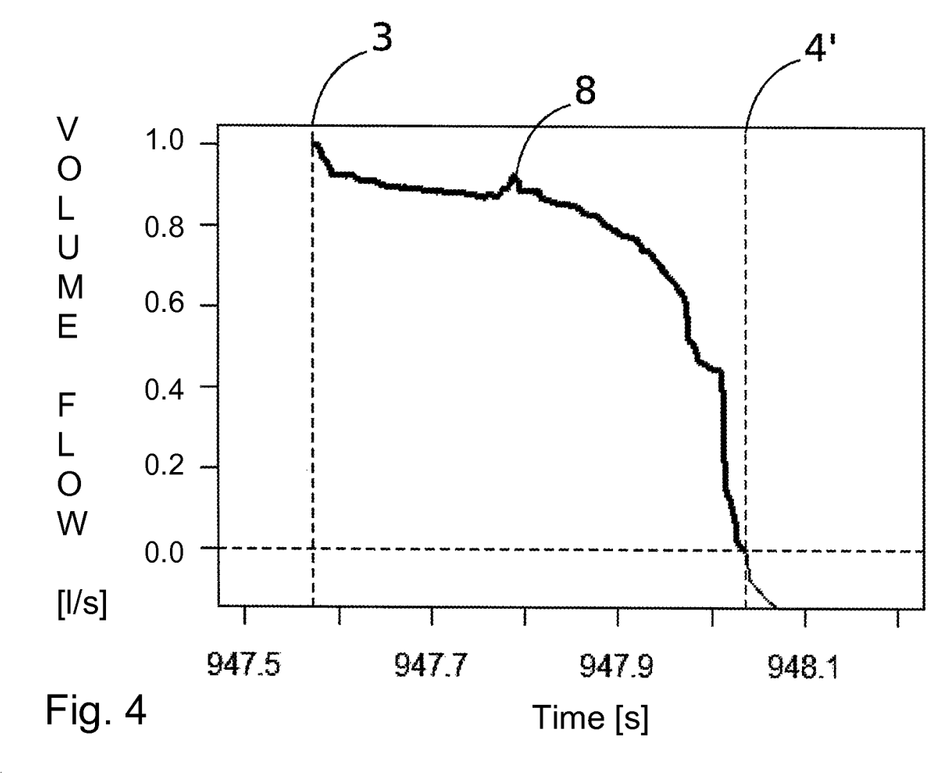
FIG. 4 is a graph of a standardized interval indicator for the non-pneumatic breathing activity signal from FIG. 3 at its threshold variable.

FIG. 4 shows the standardized interval indicator for the EMG signal from FIG. 3. As explained above in reference to FIG. 2, the standardized interval indicator begins at the reference point in time 3 with the value 1. The standardized interval indicators for the pneumatic breathing activity signal from FIG. 2 and the non-pneumatic breathing activity signal from FIG. 4 are thus on an equal scale and thus can be compared with one another and combined in a suitable manner.

The standardized interval indicator 8 for the non-pneumatic EMG signal from FIG. 4 reaches the value 0 at the point in time 4'. This would thus determine the trigger point in time when only the EMG signal would be used for changing over the phases of respiration.

Figure 5:
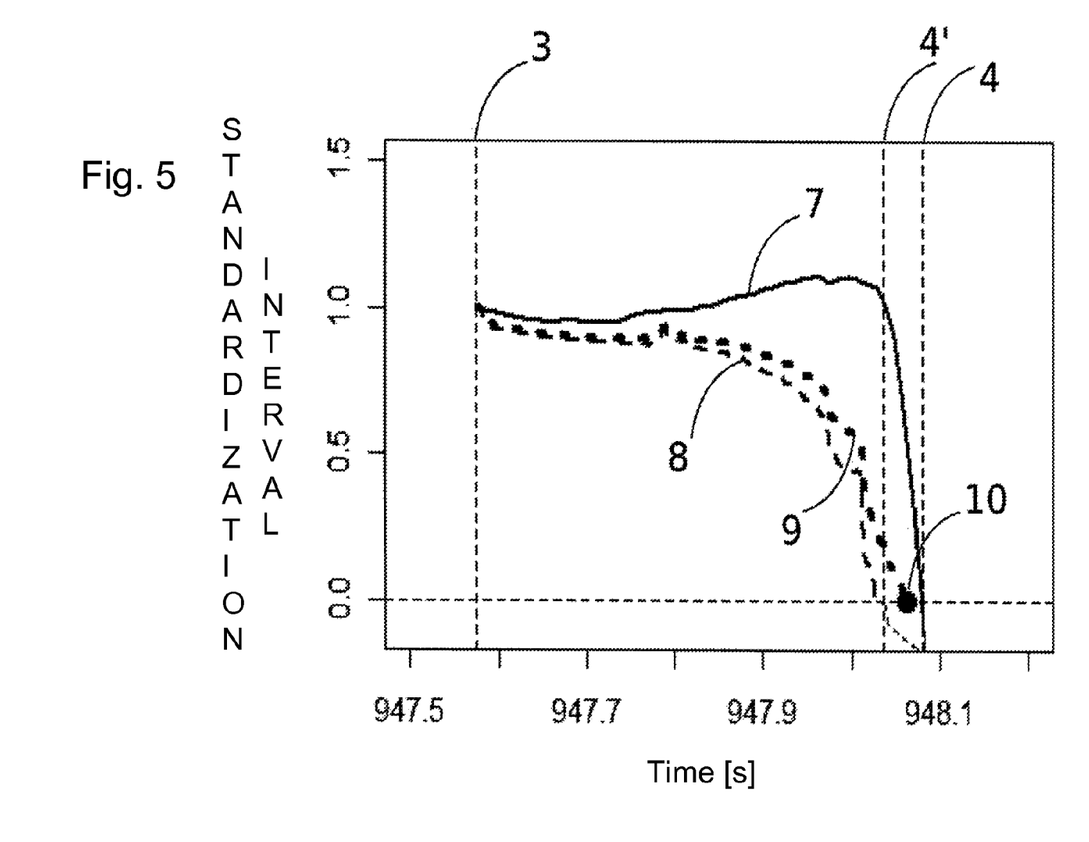
FIG. 5 is a graph of standardized interval indicators shown in FIGS. 2 and 4 as well as a mean interval indicator formed therefrom as a function of time over a phase of expiration.

The standardized interval indicators 5 and 6 from FIGS. 2 and 4 are summarized in a view in FIG. 5. It can be seen that the interval indicators do not become 0 at the same point in time; in the present case, the interval indicator 8 for the EMG signal reaches the value 0 at an earlier point in time 4' than the interval indicator 7 for the volume flow signal, which reaches the value 0 at the point in time 4. In conventional processes, it would now be determined beforehand which breathing activity signal shall supply the trigger for changing over the phases of respiration; thus, the changeover from expiration into inspiration would be done either at the point in time 4' (using the EMG signal as the trigger) or at the point in time 4 (using the volume flow signal for triggering the next inspiration).

According to the present invention, the two interval indicators are averaged or combined into a mean interval indicator. Herein, a simple arithmetic average may be formed; however, other averagings, such as geometric or harmonic mean value, median or minimum or maximum of both can be used. It is, however, preferred not to perform a simple arithmetic mean value formation, but rather to form a weighted average. The weighting should give that interval indicator more weight that corresponds to the one of the pneumatic and non-pneumatic breathing activity signals that has the higher signal quality. Such a mean value formation with weighting factors on a signal quality basis can then thus be formed:

$$K(t) = \frac{Q_{non-pneu}}{Q_{non-pneu} + Q_{pneu}} \cdot \delta_{non-pneu}(t) + \frac{Q_{pneu}}{Q_{non-pneu} + Q_{pneu}} \cdot \delta_{pneu}(t),$$

wherein $Q_{pneu}$ is a quality indicator for the pneumatic breathing activity signal and $Q_{non-pneu}$ is a quality indicator for the non-pneumatic breathing activity signal. Such a weight average on a signal quality basis was performed in the example from FIG. 5, whereby in the present example this led to a weighting of 80% for the EMG signal and 20% for the flow signal. Among other things, this leads to the zero crossing for the combined interval indicator at 8 to be closer to the zero crossing 4' for the EMG signal than to the zero crossing 4 for the flow signal.

$$Q_{flow} = \max\{0, 1 - V_{leak}/V_{exp}\}.$$

can be selected, for example, as a quality indicator for the flow signal.

Herein, $V_{leak}$ is the outflowing volume that flows out due to a leak. In case of a minimal leak, this quality indicator comes close to the value 1. In case of a larger leak that produces a $V_{leak}$ close to the expiratory volume, the quality indicator comes close to the value 0. Also, alternative quality indicators can be defined, which take into account, for example, the interference of condensed water in the hose system or cardiogenic oscillation. This is possible by determining the signal powers in higher frequency ranges, e.g., by means of Fourier transformation and relating them to a reference power (or signal power in the respiratory rate range).

The degree of suppression of artifacts (e.g., QRS complexes, i.e., deflections and peaks of an ECG signal) as well as the ratio of the mean activity of the signal during breathing in to the mean activity during breathing out are suggested as quality indicators for the EMG envelope signal.

The degree of extinguishing or suppression of artifacts—here especially of QRS complexes—can be determined, for example, as a power ratio $Q_{QRS}=\min\{1,P_{mean}/P_{QRS}\}$. $P_{QRS}$ designates the mean signal power in past time windows, the QRS complexes included. By contrast, $P_{mean}$ is the total mean power. The mean powers can be calculated, for example, as RMS values of the signal divided by the length of the time interval, over which the RMS calculation is performed. $Q_{QRS}$ is 1, when $P_{QRS}$ is not greater than the mean power $P_{mean}$, which means that the artifacts practically supply no more contribution to the mean activity, i.e., they are sufficiently extinguished. By contrast, when $P_{QRS}$ is considerably greater than the mean power $P_{mean}$, the value of the indicator $Q_{QRS}$ is about 0.

As an alternative, the total mean power $P_{mean}$ can be compared to the power during the inspiration $P_{insp}$. The corresponding quality indicator is then $Q_{insp}=\max\{0,1-P_{mean}/P_{insp}\}$. $Q_{insp}$ is about 1, when the power during the inspiration $P_{insp}$ is considerably greater than the mean power $P_{mean}$. Inversely, $Q_{insp}$ reaches the value 0, when the power during the inspiration $P_{insp}$ is not greater than the mean power $P_{mean}$.

Correspondingly, the total mean power $P_{mean}$ can be compared to the power during the expiration $P_{exp}$. The quality indicator is then $Q_{exp}=\max\{0,1-P_{mean}/P_{exp}\}$. $Q_{exp}$ reaches the value 1, when the power during the expiration $P_{exp}$ is considerably greater than the mean power $P_{mean}$.

These quality indicators quantify the distinguishability of an inspiratory or expiratory effort of the mean activity and represent a type of standardized signal/noise ratio. Only if a good distinguishability is given, i.e., when the mean inspiratory activity is higher or the mean expiratory activity is lower than the mean activity, is the use of such an EMG envelope signal for triggering advisable.

A prerequisite for the valid determination of such a quality indicator is that the breathing phases are respectively clearly determined by the analysis of pneumatic signals because only then are the time windows for the determination of the powers known. In practice, it is suggested to determine the mean EMG envelope signal powers while adjusting CPAP respiration, i.e., while omitting assisted strokes. As a result of this, a possible asynchronicity is avoided or even a high assistance suppresses the EMG activity too much. The omitting of individual assistance strokes can be done by a transient maneuver at the respirator.

To represent a quality indicator for the EMG envelope signal, for example, a combination of the previously mentioned quality indicators may also be provided, for example, as a product $$Q_{emg}=Q_{insp}\cdot(1-Q_{exp})\cdot Q_{QRS}$$

$Q_{emg}$ reaches the value 1, when the inspiratory activity of the EMG envelope signal is high and the expiratory activity is low compared to the mean activity, and QRS artifacts have been successfully extinguished. The above-mentioned condition that the inspiratory activity is high and expiratory activity is low compared to the mean activity means that the inspiration with an increased muscle activity in the case of breathing effort reflects increased signal activity, while this is not the case in expiration, which is consistent with the assumption that the EMG envelope signal is actually an image of the muscle activity.

As an alternative to the product formation shown above, the individual quality indicators could also be combined by weighted averaging:

$$Q_{emg}=\alpha_1 Q_{insp}+\alpha_2(1-Q_{exp})+\alpha_3 Q_{QRS}$$

wherein the sum of the weights $\alpha_i$ yields the value 1. When this combined quality indicator shall be used respectively for the assessment of the inspiratory trigger criteria, the influence of $Q_{insp}$ is taken to be more important than $Q_{exp}$, because an increased expiratory activity is not very relevant for inspiratory triggering. In this sense, $\alpha_i$ could be selected to be considerably greater than $\alpha_2$.

Furthermore, quality indicators can be defined that assess the variability of breathing cycles. This can be reached, respectively, by determining the variability of past breath durations (e.g., by means of calculating the standard deviation) related to the mean breath duration. While a very low variability appears to be pathological, a very high variability is an indication of asynchronicity and increased breathing work possibly as a result of an incorrect respiration adjustment.

Further possible quality indicators are based on the correlation coefficients, correlation function, mutual information or on another statistical indicator for determining correlation properties among various respiratory signals. As an example, the correlation coefficient between the flow signal and the signal of strain gauges (attached to the thorax) would have to be very high, since both signals detect the change in the thoracic volume to a considerable extent. If the correlation coefficient has only a low value, either the flow signal or the signal of the strain gauges (or both signals) is being interfered with. If, respectively, the flow signal from another side is estimated to be reliable, the signal of the strain gauges must be assumed to have a low quality.

As described above, the weighted arithmetic mean, but also the (possibly weighted) geometric or harmonic mean value as well as the (possibly weighted) median are suitable as further possibilities for the combination of such quality indicators.

The quality indicators may be quantified before their combination, i.e., be divided into intervals (e.g., into categories such as low=[0, 0.3], medium=[0.3, 0.7] and high=[0.7, 1.0]). The quality indicators may, furthermore, be subject to a threshold value switching, such that a quality indicator respectively then has an active influence on the combination if it has exceeded a minimum value.

Furthermore, the use of a fuzzy controller is suggested for analyzing the combination of quality indicators, especially when many quality indicators and possibly other influence variables, which may also be inconsistent, shall be combined with one another. The use of fuzzy controllers is state of the art and will not be described further here.

Figure 6:
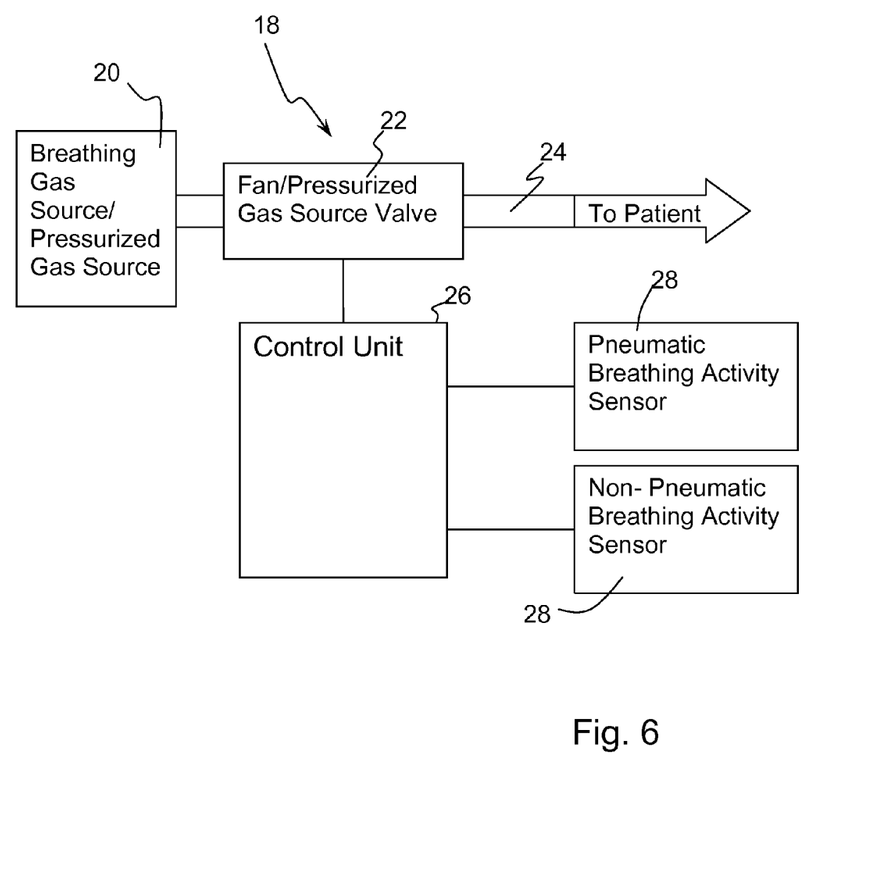
FIG. 6 is a schematic view of a respirator according to the invention.

FIG. 6 shows a respirator 18 with a breathing gas source/pressurized gas source 20 connected to a fan/controllable respiratory gas pressure supply valve 22 for conveying breathing gas through connection lines 24 to a patient. A control unit 26 controls the fan/valve 22. Sensors 28 are connected to the control unit 26 for picking up at least one pneumatic breathing activity signal and at least one non-pneumatic breathing activity signal. The sensors 28 are connected to the control unit 26. The control unit controls the respirator in accordance with the described process for a consecutively made changeover between inspiration and expiration phases of respiration including controlling the fan of the respirator when changing over into a new phase of respiration, such that a pneumatic respiration variable is brought from an actual value to a preset target value for the new phase of respiration.

While specific embodiments of the invention have been shown and described in detail to illustrate the application of the principles of the invention, it will be understood that the invention may be embodied otherwise without departing from such principles.

What is claimed is:

1. A process for the automatic control of a respirator having a fan or a controllable respiratory gas pressure supply, a control unit controlling the fan or the respiratory gas pressure supply for a changing over between consecutive inspiration and expiration phases of respiration and sensors for detecting a pneumatic breathing activity signal $u_{pneu}(t)$ and a non-pneumatic breathing activity signal $u_{non-pneu}(t)$, the sensors being connected to the control unit for transmitting measured signals, the process comprising the steps of:

picking up a pneumatic breathing activity signal $u_{pneu}(t)$ and a non-pneumatic breathing activity signal $u_{non-pneu}(t)$ of a patient;

determining intervals $\Delta_{pneu}(t)$ and $\Delta_{non-pneu}(t)$ to associated threshold variables starting from a preset reference point in time since the beginning of a present phase of respiration;

standardizing the intervals $\Delta_{pneu}(t)$ and $\Delta_{non-pneu}(t)$ to one another at standardized intervals $\delta_{pneu}(t)$ and $\delta_{non-pneu}(t)$, such that the standardized intervals $\delta_{pneu}(t)$ and $\delta_{non-pneu}(t)$ have equal interval values at the preset reference point in time;

averaging the standardized intervals $\delta_{pneu}(t)$ and $\delta_{non-pneu}(t)$ to a mean interval indicator; and changing over into a next phase of respiration when a combined interval indicator is 0.

2. A process in accordance with claim 1, wherein the pneumatic breathing activity signal $u_{pneu}(t)$ is selected from among airway pressure, flow, and volume.

3. A process in accordance with claim 1, wherein the non-pneumatic breathing activity signal $u_{non-pneu}(t)$ is selected from among respiratory muscle pressure, esophageal pressure, pressure over the stomach, electric EMG signals, MMG signals, thoracic impedance signals, FEIT signals, and from geometric chest belt signals, abdominal belt signals and strain gauge signals, motion signals, acceleration sensor signals, and acoustic signals and microphone signals.

4. A process in accordance with claim 1, wherein the standardized interval to the threshold variable for the pneumatic breathing activity signal is determined by $$\delta_{pneu}(t) = \frac{u_{pneu}(t) - u_{pneu,thresh}(t)}{u_{pneu\ ref} - u_{pneu,thresh}(t)},$$

wherein $u_{pneu\ ref}$ is the pneumatic breathing activity signal at the preset reference point in time of the present phase of respiration.

5. A process in accordance with claim 1, wherein the standardized interval to the threshold variable for the non-pneumatic breathing activity signal is determined by $$\delta_{non-pneu}(t) = \frac{u_{non-pneu}(t) - u_{non-pneu,thresh}(t)}{u_{non-pneu\ ref} - u_{non-pneu,thresh}(t)},$$

wherein $u_{non-pneu\ ref}$ is the non-pneumatic breathing activity signal at the preset reference point in time of the present phase of respiration.

6. A process in accordance with claim 1, wherein a flow signal $\dot{V}(t)$ is used as the pneumatic breathing activity signal and the standardized interval to the associated threshold variable is determined by $$\delta\dot{V}(t) = \frac{\dot{V}(t) - \dot{V}_{thresh}(t)}{\dot{V}_{ref} - \dot{V}_{thresh}(t)},$$

wherein $\dot{V}_{ref}$ is the value of the flow signal at the given reference point in time in the present phase of respiration.

7. A process in accordance with claim 1, wherein an electromyographic signal EMG(t) is used as the non-pneumatic breathing activity signal and the standardized interval to the associated threshold variable is determined by $$\delta EMG(t) = \frac{EMG(t) - EMG_{thresh}(t)}{EMG_{ref} - EMG_{thresh}(t)},$$

wherein $EMG_{ref}$ is the EMG signal at the given point in time in the present phase of respiration.

8. A process in accordance with claim 1, wherein the combined interval indicator is formed from the standardized intervals $\delta_{pneu}(t)$ and $\delta_{non-pneu}(t)$ as a weighted arithmetic, geometric or harmonic mean value, as a weighted median, as a minimum or as a maximum.

9. A process in accordance with claim 8, wherein the combined interval indicator is determined by the equation:

$$K(t) = \frac{Q_{non-pneu}}{Q_{non-pneu} + Q_{pneu}} \cdot \delta_{non-pneu}(t) + \frac{Q_{pneu}}{Q_{non-pneu} + Q_{pneu}} \cdot \delta_{pneu}(t),$$

wherein $Q_{pneu}$ is a quality indicator for the pneumatic breathing activity signal and $Q_{non-pneu}$ is a quality indicator for the non-pneumatic breathing activity signal.

10. A process in accordance with claim 1, wherein a plurality of non-pneumatic breathing activity signals $u_{non-pneu,\ i}(t)(i=1,\ \ldots\ n)$ of a patient are detected, and the interval $\Delta_{non-pneu,\ i}(t)$ and the standardized interval $\delta_{non-pneu,\ i}(t)$ are determined for each, respectively, and all intervals $\delta_{pneu}(t)$ and $\delta_{non-pneu,\ 1}(t)$ are averaged to the mean interval indicator and a changeover is made into the next phase of respiration when the combined interval indicator is 0.

11. A process in accordance with claim 10, wherein the combined interval indicator is determined by the equation:

$$K(t) = \sum_{i=1}^{n} \frac{Q_{non\text{-}pneu,i}}{\sum_{j=1}^{n} Q_{non\text{-}pneu,j} + Q_{pneu}} \cdot \delta_{non\text{-}pneu,i}(t) +$$

$$\frac{Q_{pneu}}{\sum_{j=1}^{n} Q_{non\text{-}pneu,j} + Q_{pneu}} \cdot \delta_{pneu}(t),$$

wherein $Q_{pneu}$ is a quality indicator for the pneumatic breathing activity signal and $Q_{non\text{-}pneu,i}$ is a quality indicator for the non-pneumatic breathing activity signal $u_{non\text{-}pneu,i}(t)$ (i=1, ... n).

12. A respirator comprising:
   a fan or a controllable respiratory gas supply;
   a control unit controlling the fan or the respiratory gas pressure supply for performing consecutive phases of inspiration and expiration; and
   sensors for detecting a pneumatic breathing activity signal $u_{pneu}(t)$ and a non pneumatic breathing activity signal $u_{non\text{-}pneu}(t)$, said sensors being connected to the control unit for transmitting measured signals, said control unit controlling the respirator for a changing over between consecutive inspiration and expiration phases of respiration, wherein said control unit is configured to:
   receive the pneumatic breathing activity signal $u_{pneu}(t)$ and the non-pneumatic breathing activity signal $u_{non\text{-}pneu}(t)$ of a patient;
   determine intervals $\Delta_{pneu}(t)$ and $\Delta_{non\text{-}pneu}(t)$ to associated threshold variables starting from a preset reference point in time since the beginning of a present phase of respiration;
   standardize the intervals $\Delta_{pneu}(t)$ and $\Delta_{non\text{-}pneu}(t)$ to one another at standardized intervals $\delta_{pneu}(t)$ and $\delta_{non\text{-}pneu}(t)$, such that the standardized intervals $\delta_{pneu}(t)$ and $\delta_{non\text{-}pneu}(t)$ have equal interval values at a preset reference point in time;
   average the standardized intervals $\delta_{pneu}(t)$ and $\delta_{non\text{-}pneu}(t)$ to a mean interval indicator;
   change over into a next phase of respiration when a combined interval indicator is 0.

13. A respirator in accordance with claim 12, wherein the pneumatic breathing activity signal $u_{pneu}(t)$ is selected from among airway pressure, flow, and volume.

14. A respirator in accordance with claim 12, wherein the non-pneumatic breathing activity signal $u_{non\text{-}pneu}(t)$ is selected from among respiratory muscle pressure, esophageal pressure, pressure over the stomach, electric EMG signals, MMG signals, thoracic impedance signals, FEIT signals, and from geometric chest belt signals, abdominal belt signals and strain gauge signals, motion signals, acceleration sensor signals, and acoustic signals and microphone signals.

15. A respirator in accordance with claim 12, wherein the standardized interval to the threshold variable for the pneumatic breathing activity signal is determined by $$\delta_{pneu}(t) = \frac{u_{pneu}(t) - u_{pneu,thresh}(t)}{u_{pneu\ ref} - u_{pneu,thresh}(t)},$$

wherein $u_{pneu\ ref}$ is the pneumatic breathing activity signal at the preset reference point in time of the present phase of respiration.

16. A respirator in accordance with claim 12, wherein the standardized interval to the threshold variable for the non-pneumatic breathing activity signal is determined by $$\delta_{non\text{-}pneu}(t) = \frac{u_{non\text{-}pneu}(t) - u_{non\text{-}pneu,thresh}(t)}{u_{non\text{-}pneu\ ref} - u_{non\text{-}pneu,thresh}(t)},$$

wherein $u_{non\text{-}pneu\ ref}$ is the non-pneumatic breathing activity signal at the preset reference point in time of the present phase of respiration.

17. A respirator in accordance with claim 12, wherein a flow signal $\dot{V}(t)$ is used as the pneumatic breathing activity signal and the standardized interval to the associated threshold variable is determined by $$\delta\dot{V}(t) = \frac{\dot{V}(t) - \dot{V}_{thresh}(t)}{\dot{V}_{ref} - \dot{V}_{thresh}(t)},$$

wherein
$\dot{V}_{ref}$ is the value of the flow signal at the given reference point in time in the present phase of respiration.

18. A respirator in accordance with claim 12, wherein an electromyographic signal EMG(t) is used as the non-pneumatic breathing activity signal and the standardized interval to the associated threshold variable is determined by $$\delta EMG(t) = \frac{EMG(t) - EMG_{thresh}(t)}{EMG_{ref} - EMG_{thresh}(t)},$$

wherein $EMG_{ref}$ is the EMG signal at the given point in time in the present phase of respiration.

19. A respirator in accordance with claim 12, wherein the combined interval indicator is formed from the standardized intervals $\delta_{pneu}(t)$ and $\delta_{non\text{-}pneu}(t)$ as a weighted arithmetic, geometric or harmonic mean value, as a weighted median, as a minimum or as a maximum.

20. A respirator in accordance with claim 19, wherein the combined interval indicator is determined by the equation:

$$K(t) = \frac{Q_{non\text{-}pneu}}{Q_{non\text{-}pneu} + Q_{pneu}} \cdot \delta_{non\text{-}pneu}(t) + \frac{Q_{pneu}}{Q_{non\text{-}pneu} + Q_{pneu}} \cdot \delta_{pneu}(t),$$

wherein $Q_{pneu}$ is a quality indicator for the pneumatic breathing activity signal and $Q_{non\text{-}pneu}$ is a quality indicator for the non-pneumatic breathing activity signal.

* * * * *